United States Patent [19]

Yamaguchi et al.

[11] 4,338,822
[45] Jul. 13, 1982

[54] METHOD AND APPARATUS FOR NON-CONTACT ULTRASONIC FLAW DETECTION

[75] Inventors: Hisao Yamaguchi, Akashi; Kazuo Fujisawa, Nishinomiya, both of Japan

[73] Assignee: Sumitomo Metal Industries, Ltd., Osaka, Japan

[21] Appl. No.: 191,338

[22] PCT Filed: Jun. 13, 1979

[86] PCT No.: PCT/JP79/00151

§ 371 Date: Jan. 22, 1980

§ 102(e) Date: Jan. 22, 1980

[87] PCT Pub. No.: WO80/00099

PCT Pub. Date: Jan. 24, 1980

[30] Foreign Application Priority Data

Jun. 20, 1978 [JP] Japan ................................. 53/75016
Sep. 22, 1978 [JP] Japan ................................. 53/117089

[51] Int. Cl.³ .......................................... G01N 29/04
[52] U.S. Cl. ..................................................... 73/643
[58] Field of Search ................. 73/643, 601, 600, 662

[56] References Cited

U.S. PATENT DOCUMENTS

| | | | |
|---|---|---|---|
| 3,958,128 | 5/1976 | Akutsu et al. | 356/431 |
| 3,978,713 | 9/1976 | Penney | 73/643 |
| 4,046,477 | 9/1977 | Kaule | 73/643 |
| 4,121,470 | 10/1978 | Kaule | 73/643 |
| 4,137,778 | 2/1979 | Primbsch | 73/643 |
| 4,137,991 | 2/1979 | Melcher et al. | 73/643 |
| 4,246,793 | 1/1981 | Fairand et al. | 73/643 |

*Primary Examiner*—Anthony V. Ciarlante
*Attorney, Agent, or Firm*—Wenderoth, Lind & Ponack

[57] ABSTRACT

In non-contact ultrasonic flaw detection, a pulse laser beam having a frequency in the infrared band is focused by a lens and caused to strike the material to be inspected, the ultrasonic wave generated by the shock upon the laser beam striking the material is propagated within the material to be inspected and received by an electromagnetic probe which detects the defects in the material being inspected.

7 Claims, 36 Drawing Figures

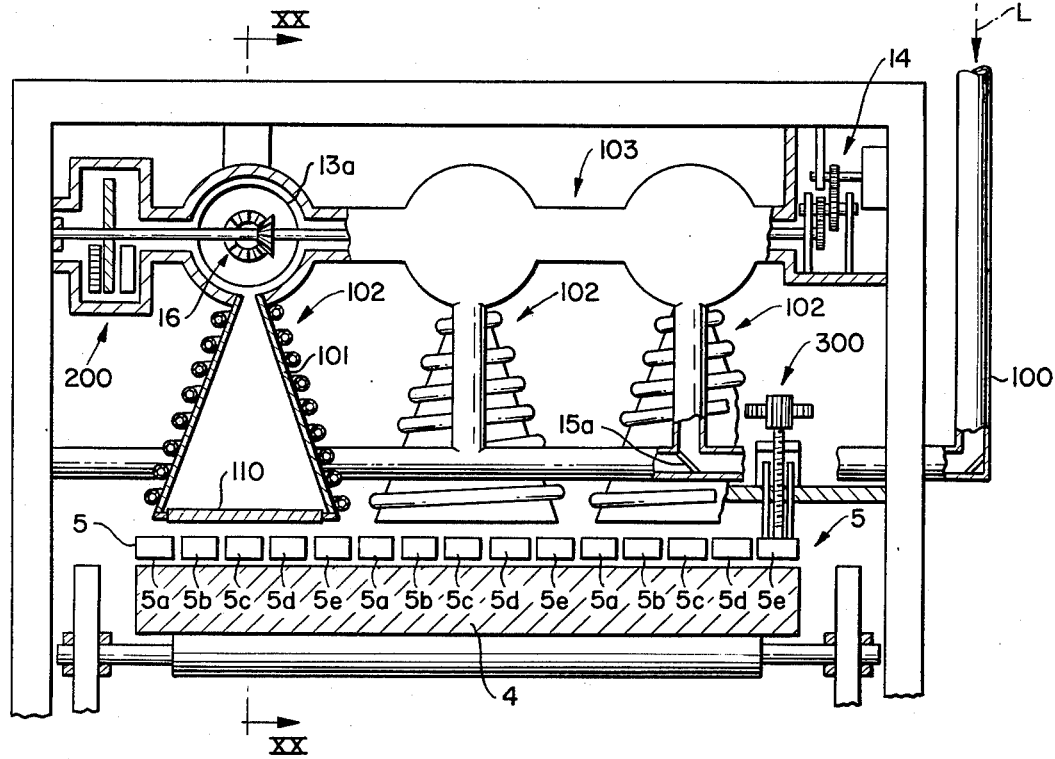
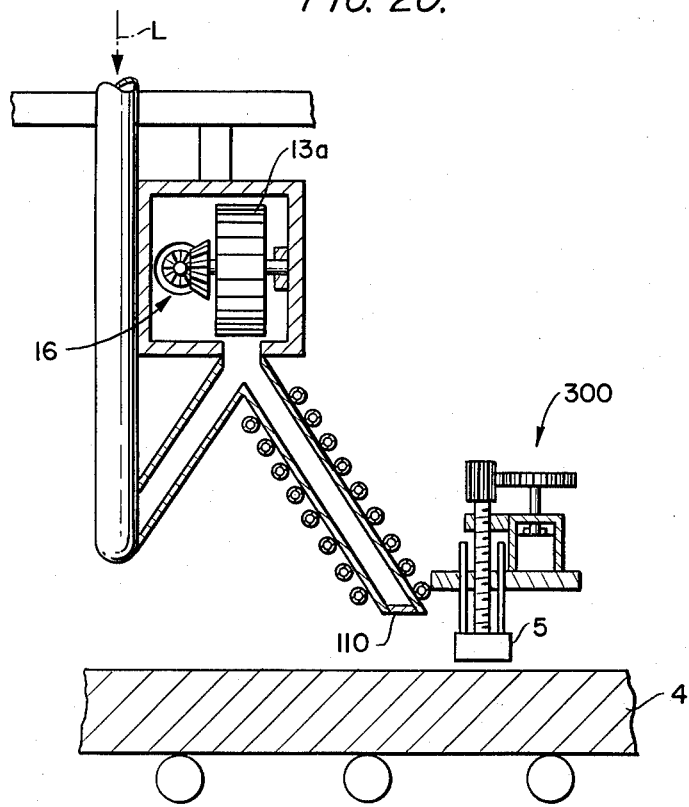

METHOD AND APPARATUS FOR NON-CONTACT ULTRASONIC FLAW DETECTION

The present invention relates to a method and apparatus for ultrasonic flaw detection for detecting defects in a material to be inspected such, for example, as steel products at high temperature, without direct contact with the material itself.

BACKGROUND ART

One of the widely used nondestructive inspection methods is ultrasonic flaw detection. In this method, however, a direct or an indirect contact between a probe and a material to be inspected through a contact medium is essential to obtain an acoustic connection between the material to be inspected and the probe for transmitting and receiving ultrasonic waves.

Ultrasonic flaw detection has been widely used as quality control means in steel material producing operations in steel mills. It has been recently attempted to perform flaw detection and scarfing conditioning of the flaw according to the results of the detection in steps as early as possible without passing any defective material to later steps, thereby increasing production efficiency and yield. For this reason, ultrasonic flaw detection of steel materials at high temperatures (800° C.–1200° C.) has been recently demanded.

However, the heretofore used common ultrasonic flaw detection methods requiring the direct or indirect contact between the probe and the hot steel material have many problems such as unduly large thermal affects from the hot steel material being inspected, thermal damage of the probe, deterioration of characteristics of the vibrator, and the like. In the flaw detection of, for example, steel materials at high temperatures (800° C.–1200° C.) during hot rolling, the heretofore used ultrasonic methods can produce little in the way of substantial results because a combustible material such as oil cannot be used as the contact medium, and other material such as water, when used as the contact medium, cannot provide a stable acoustic connection between the probe and the steel material due to rapid evaporation, and the probe itself is subjected to the very high temperatures.

As for scanning by means of a probe, the heretofore used ultrasonic flaw detection methods adopt either the system in which one probe reciprocates widthwise of the steel material or the system in which a plurality of probes are prearranged widthwise of the steel material to be inspected. Both the systems require large-scale equipment.

Non-contact ultransonic flaw detection methods have been developed to solve these problems. One of non-contact ultrasonic flaw detection methods, namely, electromagnetic ultrasonic flaw detection, will now be briefly described below.

When a static magnetic field is applied in a perpendicular or in a parallel direction with respect to the widthwise direction of a material to be inspected such as a steel material and a high frequency electric current is applied to a coil disposed opposite to the surface of the material to be inspected, ultrasonic waves are produced by Lorentz' force due to an eddy current induced on the surface of the material being inspected by the high frequency current and said static magnetic field. The ultrasonic waves are propagated through the material being inspected and are, when a defect is present, reflected or considerably attenuated by the defect before reaching the back surface of the material. In the absence of any defect, the waves are only slightly attenuated before reaching the back surface and are reflected thereby. In this way, since the ultrasonic waves reflected to the surface of the material being inspected or reaching to the back surface thereof can detect the eddy current generated by the ultrasonic vibrations and said static magnetic field applied to the front or the back surface of the material being inspected, by means of a coil disposed opposite to the front or the back surface thereof, it is possible to determine the presence of any defect and to locate it by analysis of the level and the time of reception of the ultrasonic waves, as in a pulse-echo or through-transmission method common in ultrasonic flaw detection methods using a transducer.

When the direction of the static magnetic field is parallel to the direction of movement of the surface of the material to be inspected, namely perpendicular to the widthwise direction of the surface of the material, transmission and reception of longitudinal waves is possible. On the other hand, when the direction of the static magnetic field is perpendicular to the direction of movement of the surface of the material to be inspected, namely parallel to the widthwise direction of the surface of the material, transmission and reception of transverse waves is possible.

In conventional electromagnetic ultrasonic flaw detection, since it is necessary to intensify the static magnetic field to increase the ultrasonic generation and reception levels, an electromagnet has usually been employed as the static magnetic field forming means and a very large amount of electric current is applied thereto. Such a probe requires water-cooling in order to remove the radiant heat from the material being inspected at a high temperature. The Joule heat generated in the electromagnet by passage of the large amount of current must also be removed to keep the electromagnet cooled. To cool the electromagnet it is necessary to arrange water passages as near as possible the coil of the magnet and, accordingly, to pay sufficient attention to the insulation system thereof. Therefore, the conventional electromagnetic ultrasonic flaw detection apparatus has a disadvantage that it requires a complicated cooling system, resulting in probes of large sizes. Further, when it has been necessary to use a plurality of probes of larger in size, the problem encountered has been that the density of inspection points has unavoidably become low. Generally, since the flaw detection has been performed in most cases with a plurality of probes, there has been difficulty that the source of electric current common to the electromagnets of the probes has had to be very large in scale.

OBJECTS AND BRIEF SUMMARY OF THE INVENTION

An object of the present invention is to provide a method and an apparatus for ultrasonic flaw detection capable of inspecting defects in a material to be inspected without contact therewith.

Another object of the present invention is to provide a method and an apparatus for ultrasonic flaw detection capable of scanning the surface of the material to be inspected with an ultrasonic generating point without any contact therewith.

A further object of the present invention is to provide a small size, highly efficient and durable electromagnetic ultrasonic probe for use with said ultrasonic flaw detecting apparatus.

In the non-contact ultrasonic flaw detecting method and apparatus according to the present invention, a defect of the material to be inspected is detected by focusing a pulse-like laser beam having, for example, a wavelength in the infrared band with suitable means such as a lens, directing the focused laser beam so as to be incident to the material to be inspected perpendicularly or at an angle with respect thereto, propagating an ultrasonic wave produced by a heat shock at the time of the incidence of the laser beam onto the material to be inspected therethrough, and receiving the ultrasonic wave with an electromagnetic ultrasonic probe comprising a permanent magnet and a plate-like detector coil and disposed in a position opposed to the surface of the material the same as or opposite to the surface onto which said laser beam is incident.

In the method and the apparatus according to the present invention, the laser beam is caused to be incident onto a mirror the direction of the face of which changes with time and the material to be inspected is scanned by the laser beam reflected from the mirror.

Further, in the method and the apparatus according to the present invention, a laser beam is caused to be incident to a plurality of half-mirrors disposed along the path of the beam so that each of the half mirrors reflects a portion of the laser beam incident thereto, the laser beam transmitted through the last one of the half mirrors is caused to be incident to a total reflection mirror, the laser beams reflected by the half mirrors and the total reflection mirror are caused to be incident to rotary mirrors the angle of surface of reflection of each of which with respect to the material to be inspected changes with time, and the laser beams reflected by the rotary mirror are projected upon different areas of the surface of the material to be inspected for scanning the material.

The electromagnetic ultrasonic probe used with the apparatus according to the present invention is made small in size by using as a static magnetic field forming member a rare earth magnet having a large maximum magnetic energy, thereby obtaining a static magnetic field as strong as that provided by an electromagnet and an effective cooling structure without the need for consideration of the sufficiency of electrical insulation.

BRIEF DESCRIPTION OF THE DRAWINGS

The invention will be better understood from the following description taken in connection with the accompanying drawings in which:

FIG. 19 is a front view of an embodiment of the scanning device shown in FIG. 16;

FIG. 20 is a side sectional view taken along the line XX—XX of FIG. 19;

DETAILED DESCRIPTION OF THE INVENTION

Figure 1:
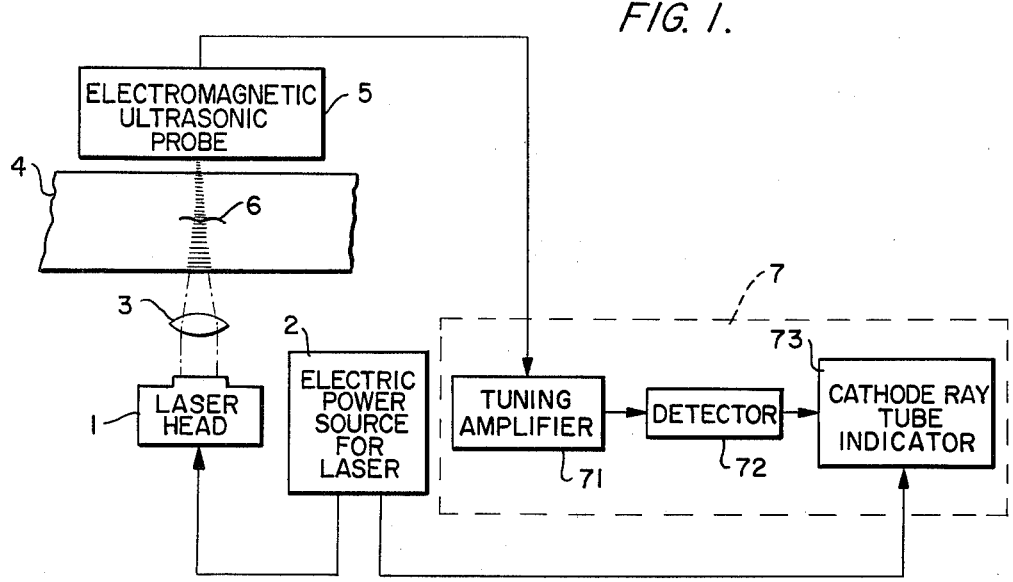
FIG. 1 is a schematic block diagram of the apparatus used in the practice of the method according to the present invention.

With reference now to the drawings, the best mode for carrying out the present invention will be described. Referring first to FIG. 1, the basic principle of the method according to the present invention will be described. Along a transfer line of a material 4 to be inspected at high temperature such, for example, as a steel material being hot rolled at temperatures 800° C.–1200° C., a pluraltiy of laser heads 1 are disposed with a predetermined distance therebetween of 10 m–20 m. Waveguides are provided for guiding laser beams and a lens 3 is provided in each waveguide between the laser head 1 and the material 4 to be inspected for focusing the pulse-like laser beam. A plurality of electromagnetic ultrasonic probes 5, each comprising a permanent magnet or an electromagnet for applying a static magnetic field to the surface of the material to be inspected and a plate-like detecting coil for detecting a displacement of the surface of the material to be inspected due to ultrasonic waves and an eddy current induced by the static magetic field due to the permanent magnet or electromagnet, are disposed opposite to the laser heads 1 on the opposite side of the surface of incidence of the laser beam but 0.5 mm–50 mm from the surface of the material to be inspected. Construction and operation of the electromagnetic ultrasonic probe 5 will be described hereinbelow in detail with reference to FIGS. 26 to 31.

The laser head 1 and an ultrasonic flaw detector 7 are connected to an electric power source 2, and the electromagnetic ultrasonic probe 5 and the ultrasonic flaw detector 7 are electrically connected to each other. The ultrasonic flaw detector 7 comprises, for example, a tuning amplifier 71, a detector 72 and a cathode-ray tube display 73, an input terminal of the tuning amplifier 71 being connected to a coil output of the electromagnetic ultrasonic probe 5 and a trigger terminal of the cathode-ray tube display 73 being connected to the electric power source 2.

The laser head 1, driven by the power from the source 2, produces a pulse-like laser beam in, for example, the infrared band which is guided by the waveguide to the surface of the material to be inspected during which the beam is focused by the lens 3 so as to be incident to the surface of the material to be inspected with an energy density required for producing ultrasonic waves. The ultrasonic waves produced by the heat shock caused on the surface of the material to be inspected by the laser beam are propagated within the material. At this time, if a defect 6 is present in the material to be inspected the ultrasonic waves are attenuated thereby. The size of the defect can be determined by detecting the degree of attenuation of the ultrasonic waves propagated through the material being inspected.

In the ultrasonic flaw detector 7, a signal from the electromagnetic ultrasonic probe 5 is amplified by the tuning amplifier 71, detected by the detector 72 and displayed by the cathode-ray tube display 73 which is synchronized with the power source 2 for laser for pulse oscillation of the laser beams of the laser head 1.

Figure 2A:
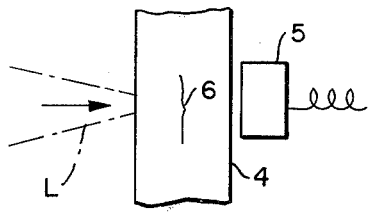
FIG. 2A is a schematic illustration of a mode of carrying out flaw detection according to the present invention.
Figure 2B:
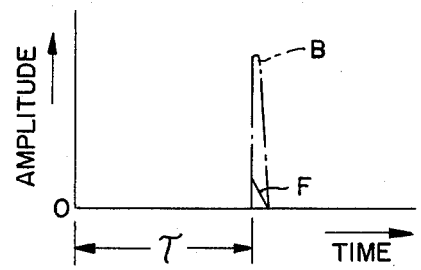
FIG. 2B is a graph showing a display of the flaw detector in the mode of FIG. 2A.

In an arrangement of the electromagnetic ultrasonic probe 5 such, for example, as shown in FIG. 2A, if the defect 6 is present in the material 4 being inspected, the cathode-ray tube display 73 displays a pulse of the form shown in FIG. 2B. When the defect 6 is not present in the material 4 being inspected, the ultrasonic pulse produced by the laser pulse is attenuated to a relatively small degree at a certain rate dependent upon the quality of the material being inspected and displayed as a reception echo B. When the defect 6 is present, the ultrasonic pulse appears as a defect reception echo F attenuated to a relatively large degree corresponding to the size of the defect. By the echo F, the presence of the defect 6 can be confirmed.

In FIG. 2B, the length $\tau$ along the horizontal axis corresponds to the length of time required for the ultrasonic wave to be propagated through the material being inspected and, accordingly, if the acoustic velocity of the material is known, the thickness of the material is determined directly from the value of $\tau$. This is firstly because the velocity of light is so far greater than the velocity of sound that the ultrasonic waves can be assumed to be generated substantially simultaneously with the generation of the laser beam, namely at the point 0 of FIG. 2B, and secondly because the reception of the defect echo by the probe 5 can be assumed to be simultaneous with the arrival of the ultrasonic wave to the surface of the material since the prove 5 detects an eddy current induced by the ultrasonic wave on the surface.

Figure 3:
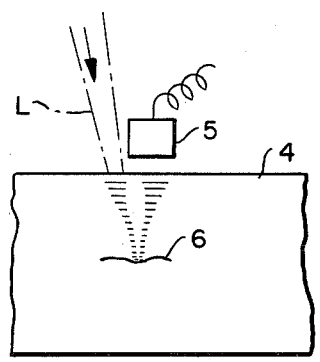
FIG. 3 is a schematic illustration of another mode of carrying out flaw detection according to the present invention.

The flaw detecting method shown in FIG. 2A is a mode of through-transmission flaw detection, in which the transmission side and the reception side are on the opposite front and back surfaces of the material to be inspected. The method according to the present invention can be practised as a pulse-echo method in which, as shown in FIG. 3, the electromagnetic ultrasonic probe 5 is disposed adjacent the point of incidence of the pulse laser beam L for receiving the ultrasonic wave reflected by the defect 6. In the pulse-echo method, the pulse laser beam L can be applied at various angles and then the echoes from the defect 6 can be received efficiently using a probe for transversal or longitudinal waves as the electromagnetic ultrasonic probe 5.

Figure 4A:
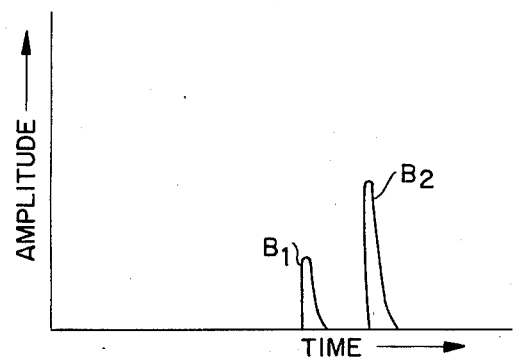
FIGS. 4A and 4B are graphs showing displays of the flaw detector in the mode of FIG. 3.
Figure 4B:
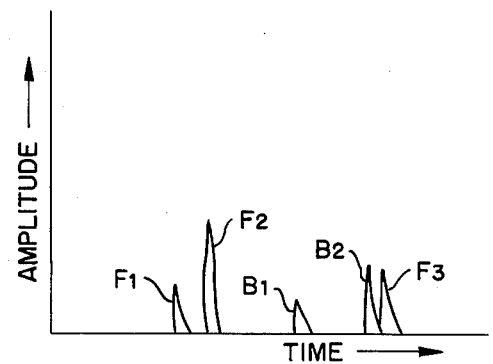
Figure 5A:
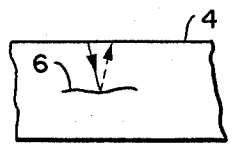
FIGS. 5A, 5B and 5C are schematic illustrations of incidence and reflection of an echo generated by a flaw.
Figure 5B:
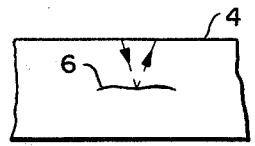
Figure 5C:
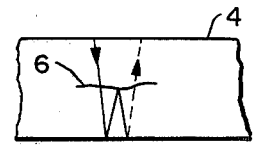

FIGS. 4A and 4B show examples of the display in the cases where the electromagnetic ultrasonic probe 5 for detection of transversal waves (see FIGS. 28 and 29) is used in the apparatus of FIG. 3. Particularly, FIG. 4A illustrates the display of the case where no defect is present and FIG. 4B illustrates the display of the case where a defect is present. In FIGS. 4A and 4B, reference character 0 denotes the point at which the laser pulse is generated, $B_1$ denotes an echo of a longitudinal wave generated at the time of the incidence of the laser beam which is then converted into a transverse wave upon reflection by the bottom of the material being inspected and received by the electromagnetic ultrasonic probe 5, $B_2$ denotes an echo of a transverse wave generated upon the incidence of the laser beam which is then reflected by the bottom of the material being inspected and received on the surface thereof. When a defect 6 is present in the central region of the material being inspected, the longitudinal and the transverse waves generated upon the incidence of the laser beam are reflected by the defect as shown in FIGS. 5A, 5B and 5C and received on the surface and displayed as echoes $F_1$, $F_2$ and $F_3$ as shown in FIG. 4B. In FIGS. 5A to 5C, solid lines denote longitudinal waves and broken lines denote transverse waves. As will be self-explanatory from FIGS. 4A and 4B, the display from the material having a defect within it is significantly different from the display from the sound material, thereby making it possible to detect such defect easily.

Figure 6A:
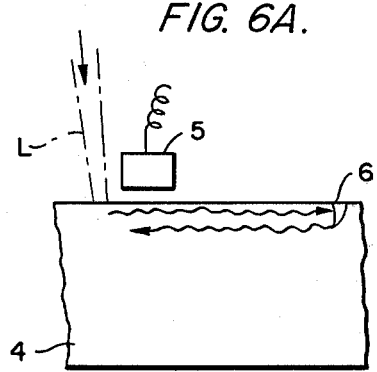
FIG. 6A is a schematic illustration of a futher mode of carrying out flaw detection according to the present invention.
Figure 6B:
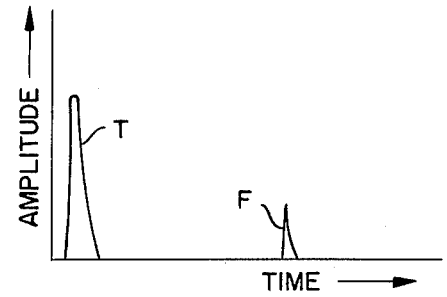
FIG. 6B is a graph showing a display of the flaw detector in the mode of FIG. 6A.

Since a surface wave is also generated by the incidence of the pulse laser beam to the material 4 to be inspected, it is possible within the scope of the present invention to carry out flaw detection for detecting surface flaws in the material 4. For example, the electromagnetic ultrasonic probe 5 for detecting surface wave may be disposed adjacent to the point at which the pulse laser beam L is incident as shown in FIG. 6A. An example of the display generated from the arrangement of FIG. 6A is shown in FIG. 6B, in which reference character T denotes a pulse detected directly by the electromagnetic ultrasonic probe 5 of a surface wave generated by the incidence of the pulse laser beam and F denotes a detected echo of the surface wave reflected by the surface defect 6. The above-described is an example of the pulse-echo method. It will be evident to those skilled in the art that it is possible within the scope of the present invention to carry out the through-transmission method.

Figure 7:
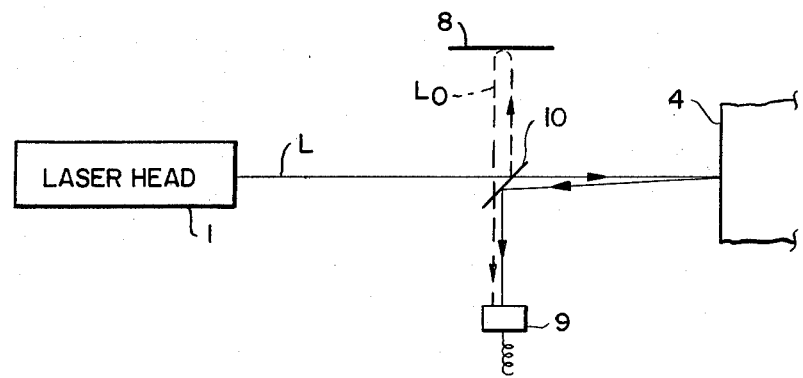
FIG. 7 is a schematic illustration of the principle of the method according to the present invention in which an ultrasonic wave is received by detecting a displacement of the surface of the material to be inspected utilizing interference of the laser beam.

As shown schematically in FIG. 7, it is also possible to receive the ultrasonic waves by detecting displacement of the surface of the material being inspected utilizing the interference phenomenon of the laser beam. In FIG. 7, reference numeral 8 denotes a total reflection mirror, 9 denotes a photoelectric multiplier, 10 denotes a half mirror, solid line arrow L denotes the path of a signal laser beam, and broken line arrow Lo denotes the path of a reference laser beam.

Assuming that the surface of the material 4 being inspected is vibrated by the ultrasonic waves, the length of the path of the signal laser beam varies. Accordingly, the interference caused between the signal laser beam L and the reference laser beam Lo the length of the path of which is fixed varies in strength corresponding to the ultrasonic vibration on the receiving surface of the photoelectric multiplier 9. By receiving the variation in strength of the interference with the photoelectric multiplier 9 it is possible to receive the ultrasonic vibration.

In the arrangement using, for example, a He-Ne laser (wavelength 0.63 $\mu$m) in which the phase difference of the optical path between the reference laser beam Lo and the signal laser beam L is zero when the surface of the material being inspected is stationary, if the surface of the material displaced $\lambda/4$ (approximately 0.15 $\mu$m) there results a phase difference $\lambda/2$ in the optical path between the reference laser beam Lo and the signal laser beam L causing them to cancel each other. Thus, when the displacement of the material being inspected is 0.15 $\mu$m, the intensity of the received light becomes zero. That is, the surface vibrating with a displacement of 0.15 $\mu$m generates a variation in the intensity of the received light from zero to the maximum. On the other hand, in the absence of the surface vibration, the intensity of the received light is always maximal. By determining the range of variation in the intensity of the received light as described above, it is possible to detect the displacement of the surface caused by the ultrasonic waves.

Since the surface of the material to be inspected is usually rough, it is necessary to focus the laser beam with a lens, to position the surface of the material to be inspected at the focus, and cause the laser beam to be incident substantially at the focal point. The amount of said displacement $\pm 0.15$ $\mu$m is larger than the range of vibration due to the ultrasonic wave used in flaw detection and, therefore, the ultrasonic wave can be received as variation in intensity of the received light. In FIG. 7, while a Michelson's interferometer is used, any other type of interferometer can be utilized.

Figure 8:
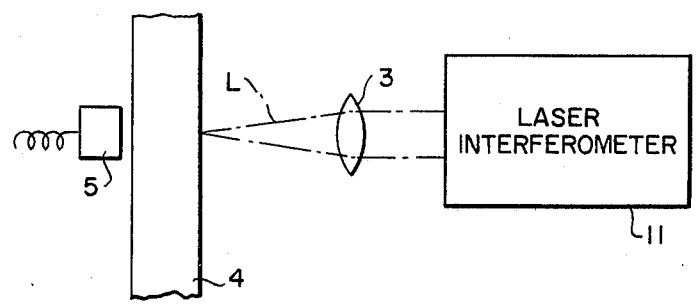
FIG. 8 is a schematic illustration of the principle of flaw detecting method according to the present invention in which an electromagnetic ultrasonic probe for longitudinal waves is used for ultrasonic transmission and a laser interferometer is used for ultrasonic reception.

FIG. 8 shows the principle of flaw detection in which the electromagnetic ultrasonic probe 5 (see FIGS. 26 and 27) for longitudinal waves is used for ultrasonic transmission and a laser interferometer 11 is used for ultrasonic reception. The ultrasonic waves transmitted by the electromagnetic ultrasonic probe 5 are propagated within the material being inspected and the displacement of the opposite surface of the material is detected by the laser interferometer 11 as the range of the variation in intensity of the received light.

Figure 9:
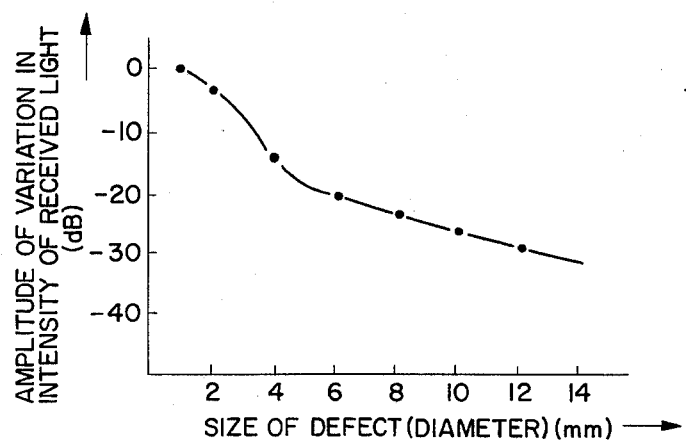
FIG. 9 is a graph showing the relation between the size of a flaw in the material to be inspected and the range of variation in intensity of the received light in the flaw detecting method of FIG. 8.

FIG. 9 shows an example of the relation between the dimension (diameter) of a flaw in the material being inspected having a thickness of 20 mm and shows the range of the variation in intensity of the received light. As shown in FIG. 9, the range of the variation in intensity decreases as the dimension of the flaw increases.

By combining this reception principle and the above-described electromagnetic ultrasonic transmission method, a flaw detection method similar to that shown in FIG. 1 can be carried out. However, this method is for detection of vertical displacement of the surface of the material and therefore limited to flaw detection using longitudinal waves.

Figure 10:
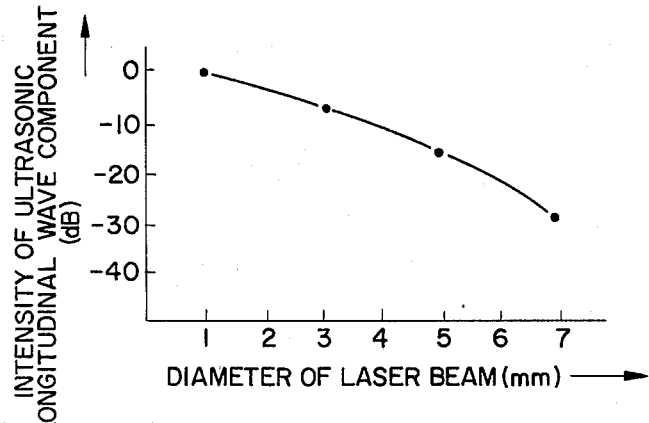
FIG. 10 is a graph showing the relation between the diameter of the laser beam and the intensity of the ultrasonic longitudinal wave.

FIG. 10 shows the experimental results for determining the relation between the diameter of the laser beam and the intensity of the ultrasonic longitudinal wave component of a sharp pulse laser Q-switched from a Nd:YAG (garnet structure) laser. As shown in FIG. 10, the strength of the longitudinal wave component is dependent upon the density of the surface energy of the laser and in order to increase the generation strength of the ultrasonic waves the surface energy density of the laser must be increased.

Figure 11:
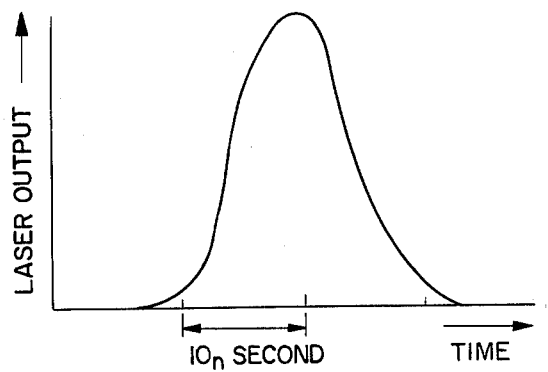
FIG. 11 is a graph showing the waveform of the pulse laser beam.

FIG. 11 shows a waveform of the Nd:YAG pulse laser. As shown in FIG. 11, a sharp rise of the wave is essential for generation of ultrasonic waves. The frequency of ultrasonic waves generated by such a pulse laser is from several ten KHz to several hundred MHz. By providing a suitable band-pass frequency filter on the reception side, flaw detection can be carried out in the optimum frequency for the particular characteristics of the material to be inspected (thickness, ultrasonic attenuation characteristic) and the size of the defect to be detected.

Figure 12:
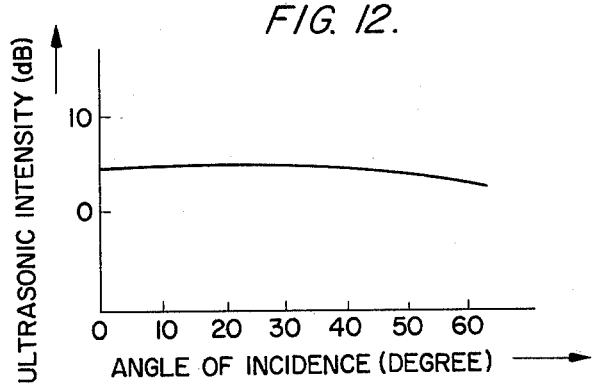
FIG. 12 is a graph showing the relation between the incident angle of the laser beam with respect to the material to be inspected and the intensity of the generated ultrasonic wave.

FIG. 12 shows the results of experiments for determining the relation between the angle of incidence of the laser beam with respect to the material and the intensity of the generated ultrasonic waves. As seen from FIG. 12, the intensity of the ultrasonic waves is substantially unrelated to the laser beam incident angle. This means that the laser beam incident angle can be changed freely by, for example, mirrors and the surface of the material to be inspected can be scanned widely.

Figure 13:
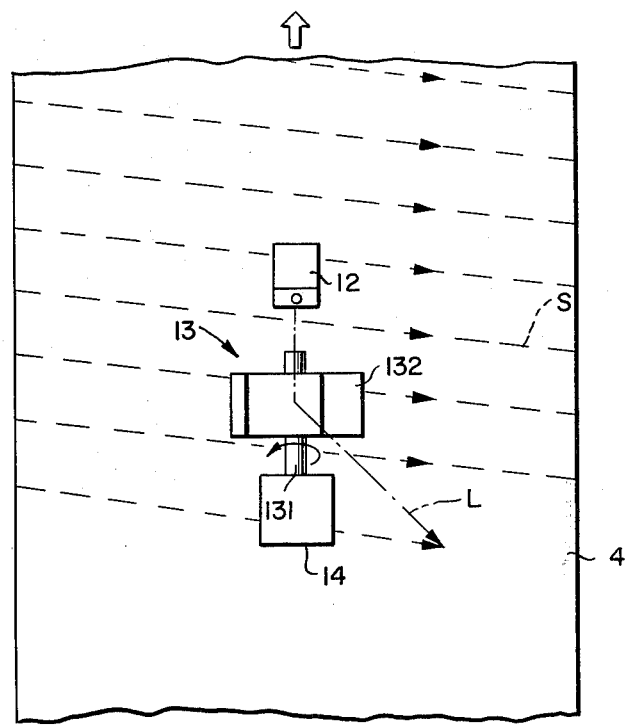
FIG. 13 is a plan view of a scanning device according to the present invention.
Figure 14:
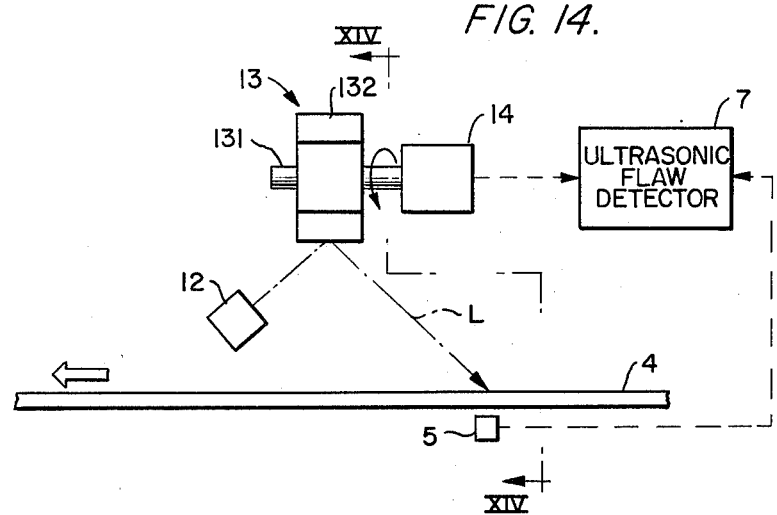
FIG. 14 is a side view of the scanning device of FIG. 13.
Figure 15:
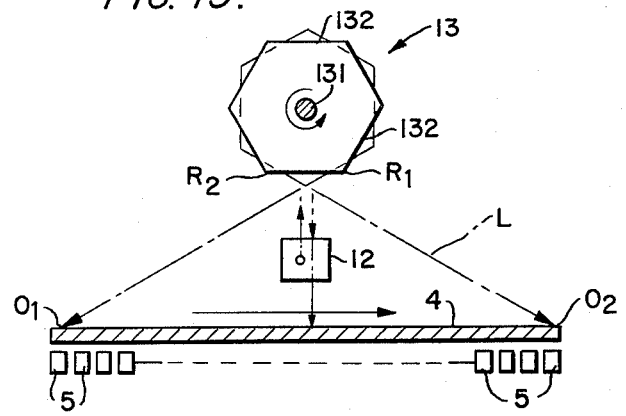
FIG. 15 is a front view taken along the line XIV—XIV of FIG. 14.

The method and apparatus for laser beam scanning of the surface of the material to be inspected using a rotary mirror will now be described. In FIGS. 13, 14 and 15, the material 4 being inspected is continuously carried in the direction indicated by a large arrow, and above a face of the material 4 (in the illustrated embodiment, the upper face) a laser generator 12, a rotary mirror 13 and a rotary driving machine 14 are fixed by a support frame (not shown).

Beneath the other face of the material 4 (in the illustrated embodiment, the underside face), a plurality of electromagnetic ultrasonic probes 5 are disposed a predetermined distances in the widthwise direction perpendicular to the direction in which the material 4 is carried.

The rotary mirror 13 has a cross-section of a regular polygonal prism (in the illustrated embodiment, a hexagonal prism) with a shaft 131 provided along the central axis thereof parallel to the direction of movement of the material 4 so that the mirror 13 is rotated by the rotary driving device 14. On the rotary mirror 13, the faces constituting the outer peripheral surface of the polygonal body thereof (in the illustrated embodiment six faces) are reflecting faces 132, respectively. As shown in FIG. 15, the rotary mirror 12 is disposed at an adequate distance from the surface of the material 4 being inspected so that the laser beam L incident to the vicinity of a forward side edge $R_1$ of the reflecting face 132 with respect to the direction of rotation of the rotary mirror 13 is reflected so as to be incident to a widthwise edge $O_1$ of the material 4 and that the laser beam L incident to the vicinity of a rearward side edge $R_2$ of the reflecting face 132 with respect to the rotating direction of the rotary mirror 13 is reflected so as to be incident to the other widthwise edge $O_2$ of the material 4.

The laser beam generator 12 is directed upwards so as to be directed at a predetermined elevation angle to the lower portion of the reflecting face 132 of the rotary mirror 13 in a vertical plane in which the shaft 131 of the rotary mirror 13 lies. The laser generator 12 consists of, for example, a Nd:YAG (garnet structure) laser having a wavelength in, for example, the infrared band, by which very short pulse-like beams are emitted for a predetermined period.

The laser beam strikes the reflecting face 132 which is moved to the underside of the rotary mirror 13 and is then reflected so as to be projected onto the surface of the material 4 being inspected. The rotary mirror 13 is rotated by the rotary driving device 14. The points to which the laser beam is projected onto the surface of the material 4 being inspected is moved gradually widthwise of the material 4 in response to the change in angle of the reflecting face 132 as shown in FIG. 15 so as to scan the surface of the material 4 along the locus S shown in FIG. 13.

In an example in which a regular polygonal prism (in the illustrated embodiment, a hexagonal prism) is rotated at the speed of 1/n Hz (in the illustrated embodiment 1/6 Hz, namely one rotation per six seconds) and the laser beam incident thereon has a pulse rate in this period of 100 Hz, then during 360°/n rotation (in the illustrated embodiment, 60°) of the rotary mirror 13, the laser beam incident thereon is deflected approximately 720°/n (in the illustrated embodiment 120°) and the laser beam striking the reflecting faces 132 is reflected thereby respectively and projected to 100 points spaced by uniform distances widthwise thereof. Accordingly, a single widthwise scanning of the material 4 to be inspected makes it possible to inspect the material at 100 spots thereon. Likewise, if the speed of rotation of the rotary mirror 13 is doubled to ⅓ Hz, a single widthwise scanning of the material 4 can inspect the material 4 at 50 spots.

The scanning range of the laser beam can be arbitrarily regulated by forming the rotary mirror 13 in the shape of a proper regular polygonal prism and disposing the mirror 13 at an adequate distance from the material 4 to be inspected. The scanning speed can be arbitrarily changed by regulating the speed of rotation of the rotary mirror 13 by regulating the speed of rotation of the rotary driving device 14. The distance between the two adjacent points at which the laser beam is projected onto the surface of the material being inspected can be arbitrarily selected by changing the emission period of the laser beam.

As described hereinabove, an ultrasonic wave is generated in the material 4 to be inspected by the impact of the laser beam. The ultrasonic wave is received and transmitted by the electromagnetic ultrasonic probe 5 to the ultrasonic flaw detector 7. A rotation synchronizing signal of the rotary mirror 13 is provided from the ultrasonic flaw detector 7 and echoes which are received corresponding to the scanning spots of the laser beams are indicated in the display device of the ultrasonic flaw detector 7.

Projection of the laser beam onto the material to be inspected is, under the above-described condition, at 100 spots. The probes 5 may be disposed beneath the material at positions corresponding to each of the projection spots or in a reduced so that one probe 5 covers several number of the projection spots. The reception of the ultrasonic waves by the probes 5 is electrically or mechanically scanned synchronously with the scanning of the laser beams.

The illustrated embodiment, in which the probes 5 are disposed on the side of the material 4 opposite to the rotary mirror 13, is for the through-transmission method. However, the probes 5 may be provided on the same side as the rotary mirror 13 for carrying out the reflection method. Further, as shown in FIG. 6A, a surface wave probe may be used for detection of surface defects. Besides, as described hereinabove, the method for detecting the displacement of the surface of the material being inspected by utilizing the phenomenon of interference of the laser beam and receiving the ultrasonic wave and any other method may be selected as required without any limitation on the ultrasonic receiving method.

As is obvious from FIG. 15, the angle of incidence of the laser beam from the rotary mirror 13 on the surface of the material 4 being inspected varies with the position of the inspecting point. It was confirmed from the experimental results shown in FIG. 12 that the variation in the angle of incidence of the laser beam has little effect on the ultrasonic generation level. In fact, as seen from FIG. 12, the decrease in the ultrasonic generation level observed to occur as the angle of incidence increases is so small that the flaw detection is hardly affected thereby.

Figure 16:
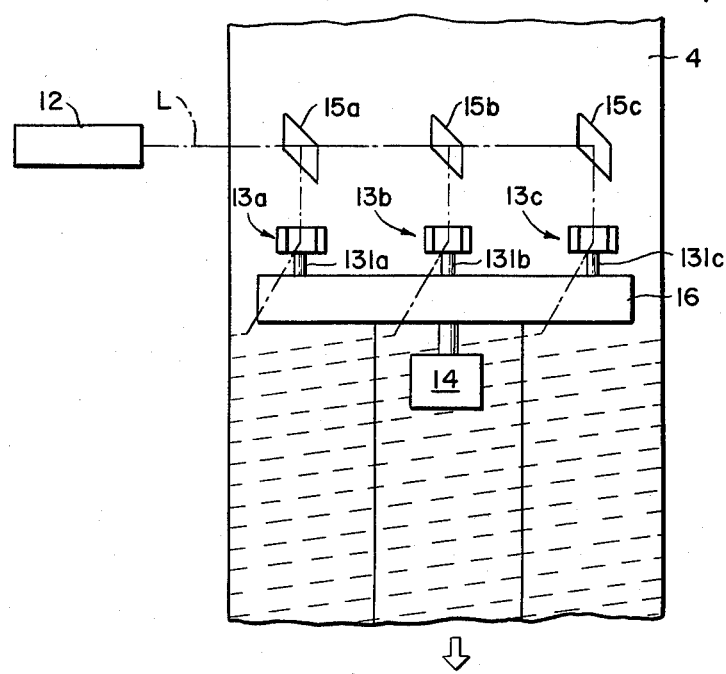
FIG. 16 is a plan view of another scanning device according to the present invention.
Figure 17:
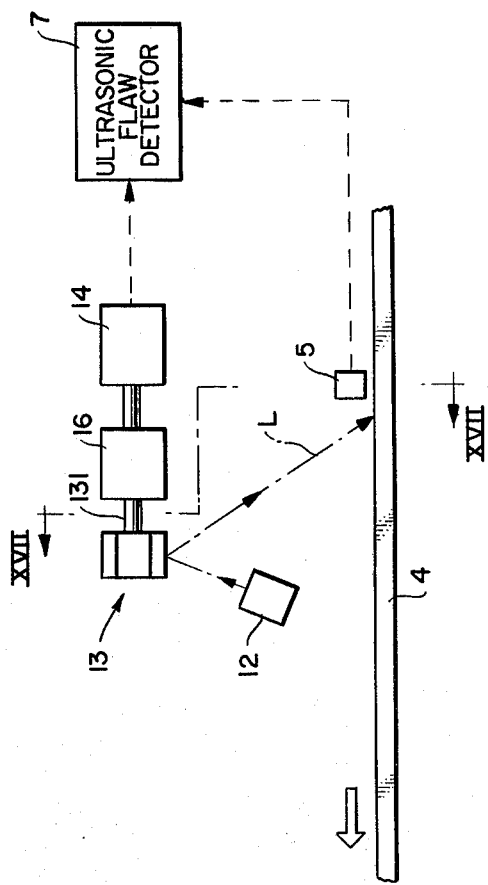
FIG. 17 is a side view of the scanning device of FIG. 16.
Figure 18:
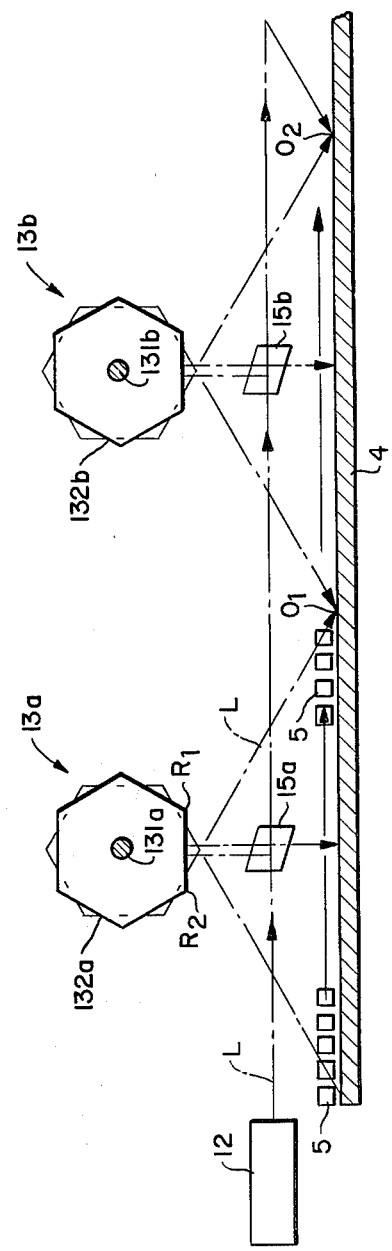
FIG. 18 is a front view taken along the line XVIII—XVIII of FIG. 17.
Figure 21:
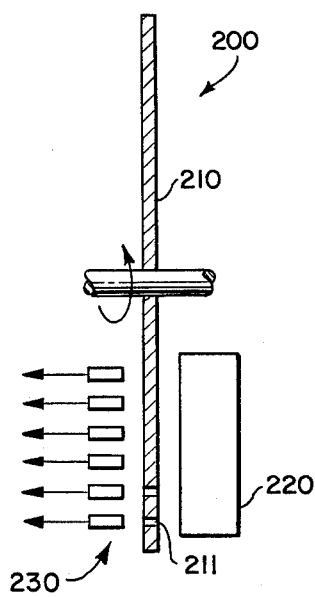
FIG. 21 is a side sectional view of a timing signal generating disk.

With reference to FIGS. 16 to 25, the method and the apparatus according to the present invention for inspecting a material has a relatively large width will now be described. FIGS. 16, 17 and 18 corresponding to FIGS. 13, 14 and 15, respectively, show the basic principle of the method and the apparatus for scanning the surface of the material to be inspected. In such drawings, like parts are denoted by the same reference numerals and characters throughout the severals views and a detailed explanation thereof will be omitted.

The method illustrated in FIGS. 16, 17 and 18 is different from the method illustrated in FIGS. 13, 14 and 15 with respect to the following four points. First, a plurality of rotary mirrors 13a, 13b, 13c . . . (three in the illustrated embodiment) are disposed widthwise of the material 4 to be inspected with a predetermined distance therebetween. Second, an interlocking device 16 for rotating the plurality of the rotary mirrors in interlocked relationship is connected between the rotary driving device 14 and the rotary mirrors 13a, 13b, 13c . . . . Third, a plurality of half mirrors 15a, 15b, 15c . . . are provided corresponding to the rotary mirrors 13a, 13b, 13c . . . , respectively, for directing the laser beam L from the laser beam generator 12 to the rotary mirrors, respectively. The mirror disposed at the terminal end of this plurality of half mirrors (in the illustrated embodiment, 15c) is preferably a total reflection mirror. Fourth, the probes 5 are disposed according to the principle of the reflection method. This, however, is merely for illustration, and the probes 5 may be disposed according to the principle of the through-transmission method as shown in FIG. 15.

As best shown in FIG. 16, the laser beam L emitted from the laser beam generator 12 strikes a reflector group consisting of a plurality of (two in the illustrated embodiment) aligned half mirrors 15a and 15b and one total reflection mirror 15c disposed along the path of the laser beam L at an angle (45° in the illustrated embodiment) thereto. The half mirrors 15a, 15b and the total reflection mirror 15c are disposed above the center of three regions, respectively, equally divided widthwise of the material 4 to be inspected, namely in the direction perpendicular to the direction of movement of the material 4. The half mirrors 15a and 15b are made to have a transmission coefficient of ⅔ and ½, respectively. Accordingly, one-third of the energy of the laser beam L emitted from the laser beam generator 12 is reflected by the half mirror 15a. Two-thirds of the energy of the beam L is transmitted through the half mirror 15a and reaches the half mirror 15b, and half is reflected thereby or one third of the entire quantity of energy of the beam L while the other half of the quantity striking the half mirror 15b or one third of the entire energy of the beam L is transmitted through the half mirror 15b and reaches the mirror 15c and is completely reflected thereby. Thus, the quantity of the light reflected by each of the half mirrors 15a and 15b and the total reflection mirror 15c is one third of the quantity of energy of the laser beam light emitted from the laser beam generator 12. Thus, three parallel laser beams of equal energy are reflected to the underside faces of the correspondingly disposed rotary mirrors 13a, 13b and 13c, respectively.

In the illustrated embodiment, the reflector group is shown to consist of three elements, namely two half mirrors and a total reflection mirror. In general, the reflector group may consist of n elements, namely n−1 half mirrors and a total reflection mirror. In this general arrangement, by making the transmission factors of the half mirrors successively positioned along the path of the laser beam L $n-1/n$, $n-2/n-1$, . . . ½, the laser beam L is divided equally into n parts which strike the corresponding rotary mirrors, respectively.

The illustrated embodiment is shown to utilize the total reflection mirror 15c for causing the laser beam to strike the terminal rotary mirror 13c. However, the total reflection mirror 15c may be replaced by a half mirror so that the reflector group consists of half mirrors only. In this arrangement, the half mirrors have different transmission factors from those described above. That is, the half mirrors closer to the laser generator 12 have larger transmission factors so that the quantities of the energies of the reflected light beams striking the rotary mirrors are the same as one another.

In the arrangement in which the reflector group consists of half mirrors only, a portion of the laser beam is transmitted through the half mirror replacing the total reflection mirror 15c to the outside of the reflector group. However, as will be described hereinunder, the portion of the beam that has leaked may be used as a synchronizing signal for the rotation of the rotary mirrors and the scanning operation of the probes 5.

The rotary mirrors 13a, 13b and 13c are disposed above the regions of the material 4 to be inspected, respectively, at the same distance from the half mirrors 15a and 15b and the total reflection mirror 15c, respectively, in the direction of movement of the material 4. The rotary mirrors 13a, 13b and 13c are connected to the rotary drive device 14 through the interlocking device 16 such as a timing belt or gears, so as to be rotatably driven in the same direction and at the same speed.

As shown in FIG. 18, the cross-sectional shape of the rotary mirrors 13a, 13b and 13c are formed in hexagonal prisms having on the outer peripheries thereof six reflecting surfaces 132a, 132b and 132c, respectively and having central shafts 131a, 131b and 131c thereof, respectively, disposed parallel to the direction of movement of the material 4. The laser beams L reflected by the half mirrors 15a and 15b and the total reflection mirror 15c strike the underside reflecting surfaces (the reflecting surfaces opposed to the surface of the material 4 to be inspected) 132a, 132b and 132c of the rotary mirrors 13a, 13b and 13c, respectively, and are again reflected thereby and strike the respective regions of the material 4. As the rotary mirrors 13a, 13b and 13c rotate 60° about the shafts 131a, 131b and 131c, respectively, the projection points of the reflected laser beams shift gradually over the angle of approximately 120° from one side edge $O_1$ to the other side edge $O_2$ of the respective regions.

In the illustrated embodiment, while the rotary mirrors 13a, 13b and 13c are shown to be regular hexagonal prisms, they are not limited to regular hexagonal prisms. In fact, they can be selected from other forms, such as regular octagonal prisms, regular dodecagonal prisms, or the like.

In general, when the rotary mirrors in the shape of a right polygonal prism are used, since the direction of reflection of the laser beam varies approximately 720°/n, the smaller the value of n, the wider the projection region, namely the flaw detection region, of the material 4 by the laser beam becomes, and the larger the value of n, the narrower the flaw detection region becomes. By changing the value of n, the width of the flaw detection region for each laser beam can be arbitrarily adjusted. The width of the flaw detection region can also be adjusted by changing the height of the rotary mirrors from the surface of the material to be inspected.

With reference now to FIGS. 19 to 25, the specific construction and operation of the scanning device will be described. FIGS. 19 and 20 are views substantially equivalent to FIGS. 18 and 17. FIGS. 19 and 20 specifically disclose a waveguide 100 for guiding the laser beam L along a predetermined path, the rotary mirror 13a, sector waveguides 101 for guiding laser beams reflected by the rotary mirrors, heat resisting glass 110, the rotary drive device 14, the interlocking devices 16, a timing signal generator 200, a probe supporting mechanism 300, and a cover 103 for projecting the rotary drive device the interlocking device and the rotary mirrors. These devices and mechanisms are conventional and will need no further description.

These devices and mechanisms are, while not clearly shown in the drawings, provided individually or together with suitable heat resisting and water cooling structures. For example, the waveguide 100 and the cover 103 have a double wall structure (not shown), and the sector waveguides 101 are cooled suitably by cooling pipes.

The timing signal generator 200 will now be described with reference to FIGS. 21 to 24. In this embodiment, the rotary mirror 13 is a regular octadecagonal prism and makes five steps of intermittent incremental rotation with respect to one surface of reflection 132. Thus, the timing signal generator 200 is designed to emit the pulse-like laser beam while the rotary mirror 13 is stopped. Accordingly, the timing signal generator 200 functions to insure synchronization among the stepwise incremental rotation of the rotary mirror 13, the ultrasonic oscillation point scanned by the pulse-like laser beam and the electromagnetic ultrasonic probe 5 which is the receiving point thereof.

Figure 22:
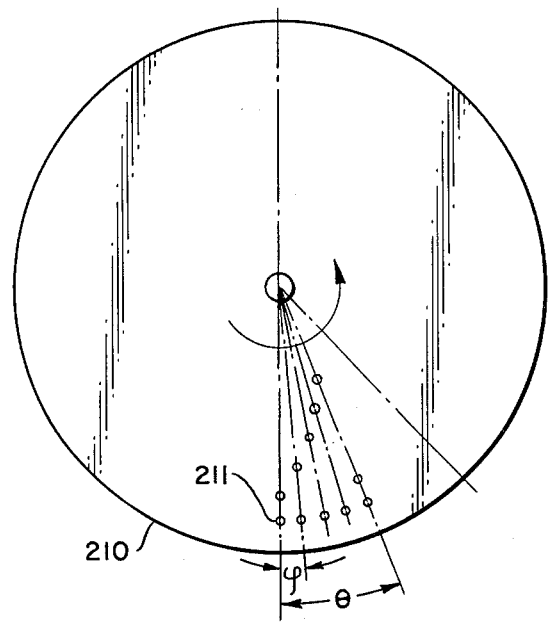
FIG. 22 is a plan view of the timing signal generating disk of FIG. 21.

The timing signal generator 200 is a conventional type comprising a rotating disk 210, a light source 220, and light detectors 230. The rotating disk 210 is connected mechanically to the rotary mirror 13 through the interlocking device 16 so as to move through the same angular displacement as the mirror 13. The rotating disk 210 is provided with a plurality of holes 211 disposed in a predetermined positional relation as shown in FIG. 22. The positional relation of the holes 211 in the rotating disk 210 is repeated for each reflection surface angle $\theta$ (in the illustrated embodiment, 20°). In a reflection signal angle $\theta$, the holes 211 are provided at positions predetermined for each stepwise incremental rotational angle $\phi$ (in the illustrated embodiment, 4°). The light beam which has passed through one of the holes 211 is detected by a corresponding one of the light detectors 230 for use by a control unit illustrated in FIG. 24.

Figure 23:
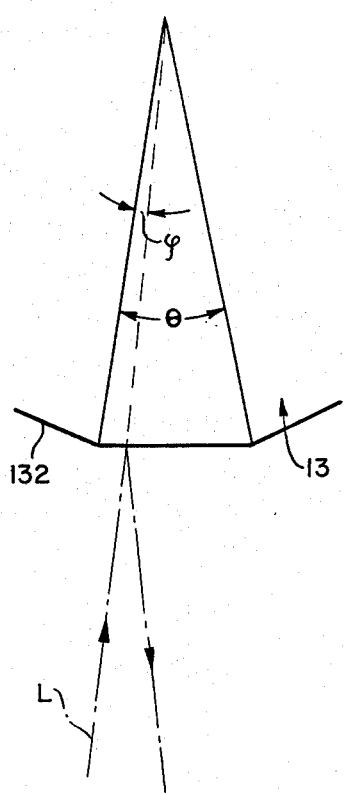
FIG. 23 is a schematic illustration of reflection of the laser beam on the surface of reflection of the rotary mirror.
Figure 25:
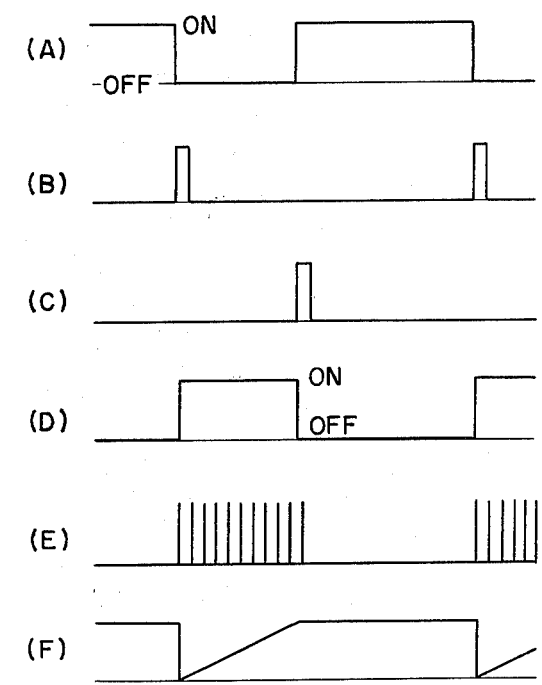
FIGS. 25A to 25F are signal diagrams for illustration of operation of the scanning device of FIG. 24.

In FIG. 23, when the reflection surface angle $\theta$ is 20° and the radius of the laser beam is approximately 8 mm, if the radius of the rotary mirror is approximately 300 mm, the stepwise incremental rotational angle $\phi$ is preferably to positions of 2°, 6°, 10°, 14° or 18° because of the presence of dead zones at the corners of the rotary mirror.

Figure 24:
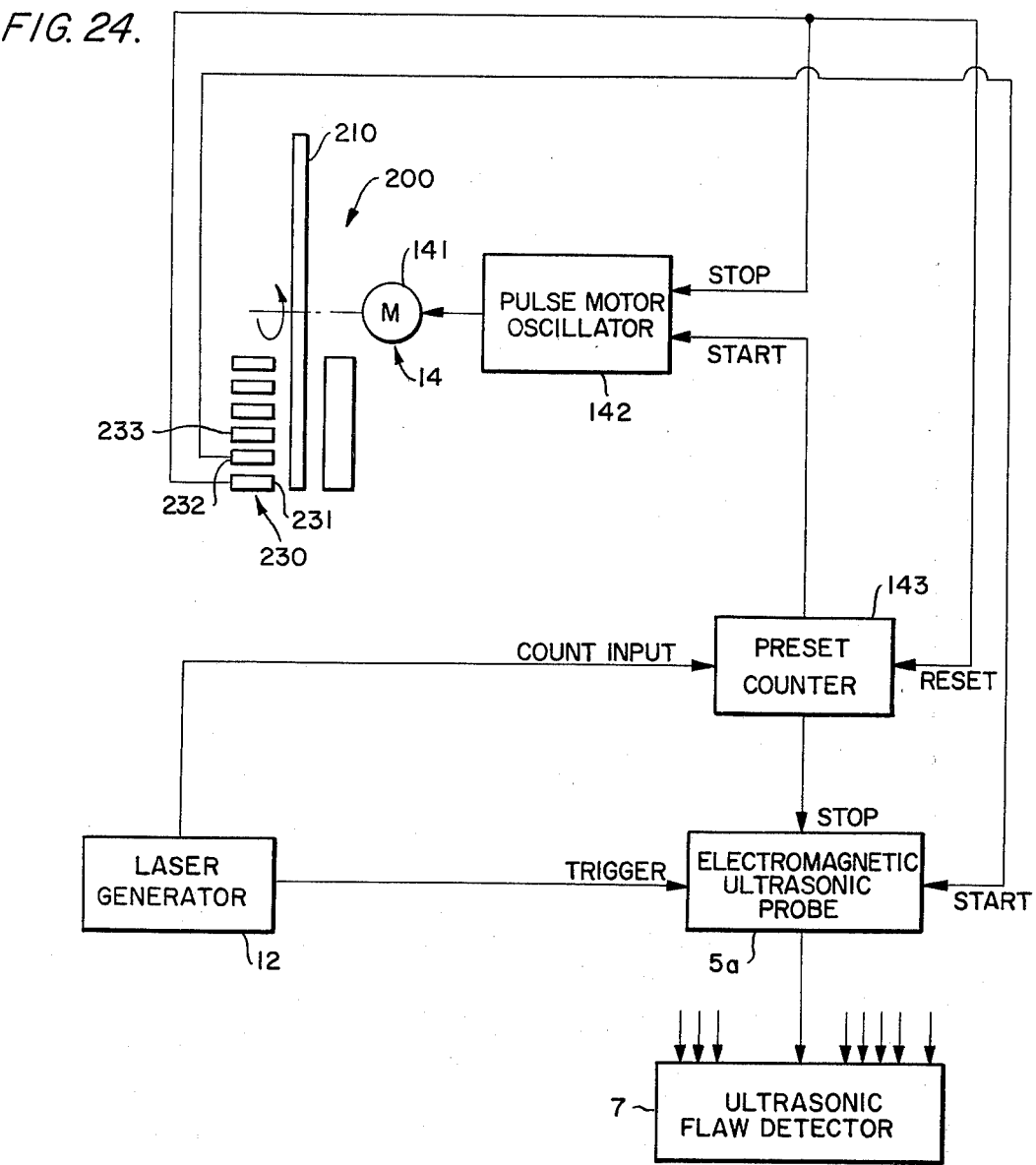
FIG. 24 is a schematic block diagram of a control unit of the scanning device of FIG. 19.

FIG. 24 shows a schematic arrangement of the scanning control unit for a single or a group of electromagnetic ultrasonic probes 5. FIGS. 25A to 25F are signal diagrams showing operation of the control unit of FIG. 24. A pulse motor 141 for the rotary driving device 14 performs a stepwise incremental rotation in response to a pulse signal (during ON in FIG. 25A) received from a pulse motor oscillator 142.

A signal (FIG. 25B) transmitted after a predetermined period from a first light detector 231 and a signal (FIG. 25C) delayed a predetermined length of time and coming from a preset counter 143 are applied to the pulse motor oscillator 142 which repeats ON-OFF conditions at a predetermined interval (FIG. 25A).

When the pulse motor 141 stops, the electromagnetic ultrasonic probe 5a receives a signal from a second light detector 232 and a signal (FIG. 25C) from the preset counter 143 and is energized to a reception mode (FIG. 25D) for a predetermined length of time. At this time, the electromagnetic ultrasonic probe 5a receives an ultrasonic pulse by a pulse laser beam L of a predetermined repetitive frequency (FIG. 25E) from the laser beam generator 12 and transmits the results of flaw detection to the ultrasonic flaw detector 7.

The preset counter 143 is reset (FIG. 25F) by a reset signal from the first light detector 231 and starts counting laser oscillation pulses from the laser beam generator 12. When the predetermined value is counted, the preset counter 143 transmits the signal (FIG. 25C) and stops counting.

Thereafter, a signal from a third light detector 233 acts as a starting signal for the electromagnetic ultrasonic probe 5b. Then, the same operation is repeated with respect to the probes 5c, 5d and 5e, successively, for each stepwise incremental rotation of the pulse motor.

Figure 26:
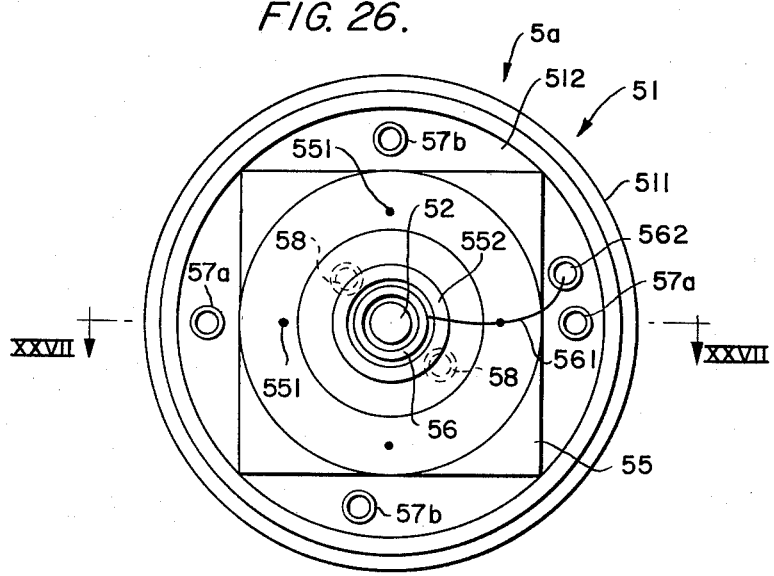
FIG. 26 is a bottom view of an electromagnetic probe for longitudinal waves for use with the apparatus according to the present invention with the bottom cover thereof removed.
Figure 27:
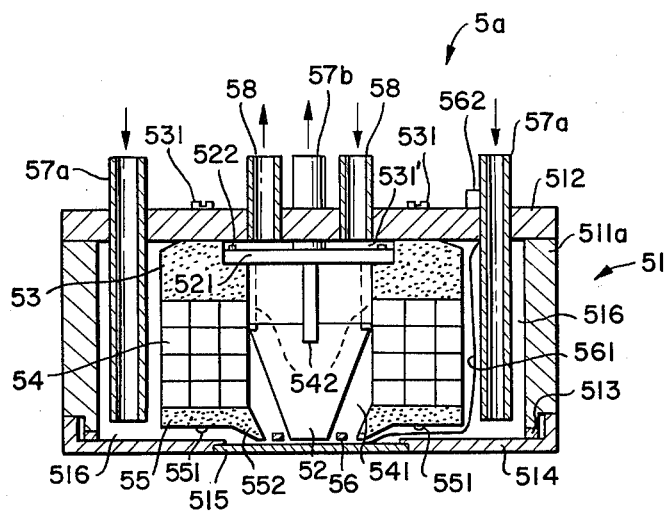
FIG. 27 is a side sectional view taken along the line XXVII—XXVII of FIG. 26.
Figure 28:
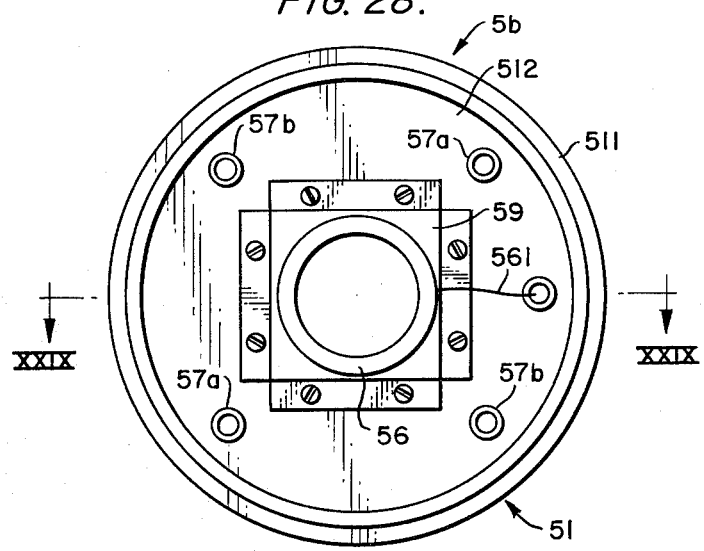
FIG. 28 is a bottom view of an electromagnetic probe for transverse waves for use with the apparatus according to the present invention with the bottom cover thereof removed.
Figure 29:
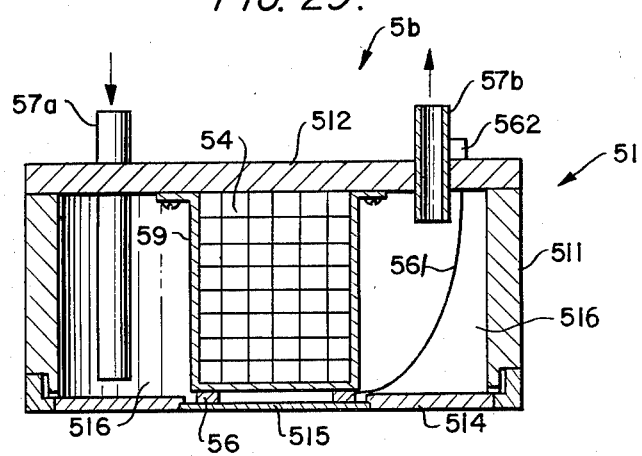
FIG. 29 is a side sectional view taken along the line XXIX—XXIX of FIG. 28.
Figure 30:
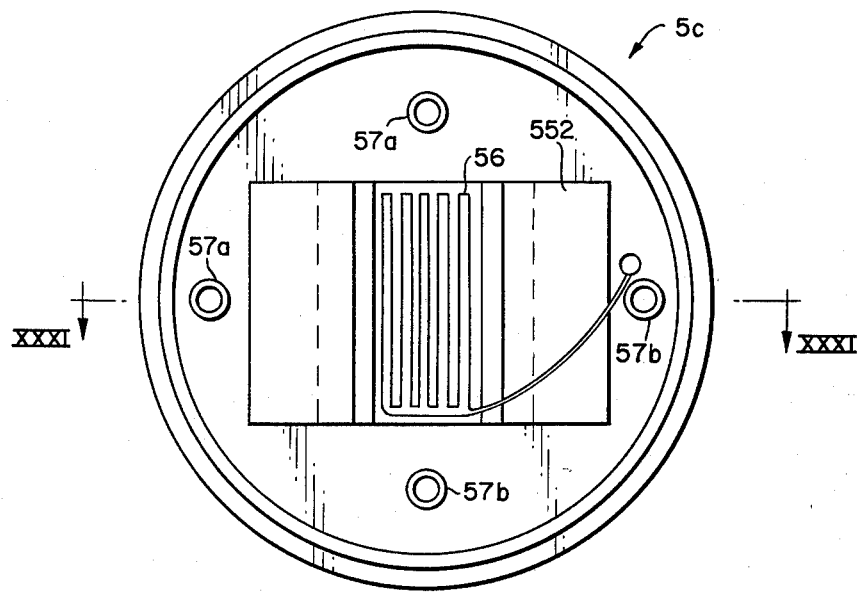
FIG. 30 is a bottom view of an electromagnetic probe for surface waves for use with the apparatus according to the present invention with the bottom cover thereof removed.
Figure 31:
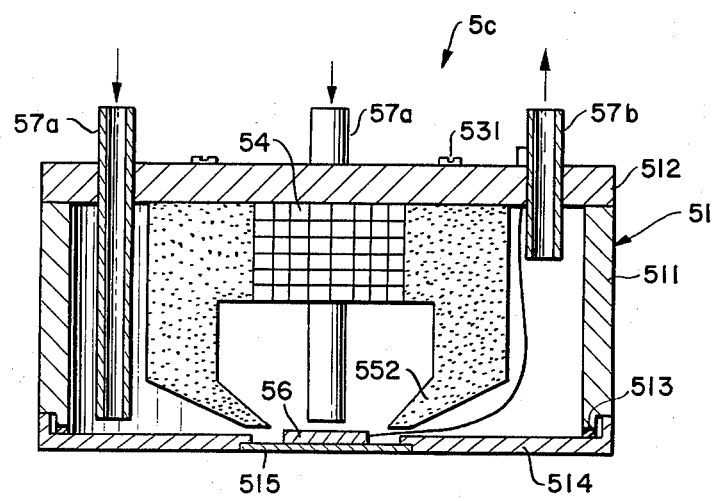
FIG. 31 is a side sectional view taken along the line XXXI—XXXI of FIG. 30.

With reference now to FIGS. 26 to 31, the electromagnetic ultrasonic probe 5 for use with the apparatus according to the present invention will be described. The probe 5a shown in FIGS. 26 and 27 is for longitudinal waves. The probe 5b shown in FIGS. 28 and 29 is for transverse waves. The probe 5c shown in FIGS. 30 and 31 is for surface waves.

In FIGS. 26 and 27, reference numeral 51 denotes a watertight case comprising a cylindrical side wall 511, a disk-like top cover 512 secured integrally to the top end of said side wall 511, a disk-like bottom cover 514 threadably secured to the lower end of said side wall 511 with a packing 513 therebetween and having a central portion thereof cut away to leave a circular opening, and a ceramic plate 515 of a highly wear- and heat-resistant material such as high alumina material fitted into the central opening in the bottom cover 514 and bonded thereto with a high temperature adhesive. The top cover 512, the side wall 511 and the bottom cover 514 are of non-magnetic material such as austenitic stainless steel or the like.

Reference numeral 52 denotes a center pole of a nonmagnetic material such as permalloy or the like, the upper half of which is a square prism having the horizontal side a little longer than one third of the internal diameter of the case and the lower half of which is downwardly tapered into an inverted conical frustum. The center pole 52 has the height a little smaller than the inside depth of the case 51 and is positioned in the center of the case so that the upper surface thereof is opposite to the central portion of the top cover 512 and the lower surface thereof is opposite to the central portion of the ceramic plate 515.

On the outer periphery of the center pole 52 are provided from above to below an upper yoke 53, a static magnetic field forming member 54, and a lower yoke 55. The upper yoke 53 is of a magnetic material in the shape of a thick ring having a central aperture with a diameter substantially equal to the horizontal side length of the upper half of the center pole 52. At the upper end of the inner wall of the upper yoke 53 is an enlarged circular stop portion to which a flange 521 formed at the upper end of the center pole 52 is fitted and that the center pole 52 and the upper yoke 53 are secured to each other by means of a plurality of set screws 522. The upper yoke 53 itself is secured to the top cover 512 by means of a plurality of set screws 531.

The static magnetic field forming member 54 is a permanent magnet generally ring-shaped, consisting of a number of small cubes of rare earth magnet material such as yttrium-iron-garnet which are tightly secured to each other with the N-poles upward and the S-poles downward and combined into a ring. The static magnetic field forming member 54 has an inside diameter of the central aperture thereof the same as that of the upper yoke 53 and a height approximately a half that of the center pole 52. The member 54 is fitted externally of the center pole 52 so as to extend from the square prismatic upper half to the inverted conic frustum lower half of the center pole 52. The member 54 has the upper surface thereof adhered to the lower surface of the upper yoke 53.

The lower yoke 55 is of a magnetic material such as permalloy and has a square thin saucer-like shape with the central portion thereof cut away to leave a circle and is supported on the lower surface of the static magnetic field forming member 54 by means of a plurality of set screws 551. The inside diameter of the central aperture of the lower yoke 55 at the upper end thereof is the same as that of the static magnetic field forming member 54 or of the upper yoke 53. However, the inside diameter of the central aperture thereof at the lower end is smaller than that at the upper end so that a lower end inner edge 552 thereof is opposite to the peripheral surface of the lower end of the center pole 52 with a relatively small clearance therebetween. In said clearance a coil 56 having a plurality of turns is disposed so as to surround the lower end of the center pole 52. Opposite ends of the coil 56 are connected, through a cable 561 extending from below the lower yoke 55 upward along the side thereof, to a connector 562 for connection to external devices.

The outside diameters of the upper and the lower yokes 53 and 55 and of the static magnetic field forming member 54, respectively, are such as to define an outer annular space 516 between the outer peripheral surfaces thereof and the side wall 511 of the case 51. The top cover 512 is provided with two long and two short water pipes 57a and 57b which are alternately disposed along the circumferential edge thereof with equal angular distance therebetween for placing the outer annular space 516 and the outside in communication. The short water pipes 57b have the lower ends thereof extending downward a little beyond the top cover 512 and the longer water pipes 57a have the lower ends thereof extending downward to near the bottom cover 514. The long water pipes 57a are connected with an external water supply (not shown) for introducing water as shown by arrows into the case 51 as a cooling medium and the short water pipes 57b are for discharging water from the case 51 as shown by arrows.

Since the lower half of the center pole 52 is on inverted frustum of a cone, an inner space 541 is defined between the lower half of the center pole and the inner peripheral surface of the static magnetic field forming member 54. On the outer peripheral surface of the prismatic upper half of the center pole 52 are an adequate number of vertical channels 542 for placing the inner space 541 in communication with a small gap 531' defined between the upper surface of the center pole 52 and the lower surface of the top cover 512. The top cover 512 is provided with two water pipes 58 disposed symmetrically with respect to the center of the top cover 512, for placing the small gap space 531 in communication with the outside. One of the water pipes 58 is connected with said water supply for introducing water into the case 51 as shown by an arrow while the other of the water pipes 58 discharges water from the case as shown by an arrow. In place of the vertical channels 542, water holes may be provided in the center pole 52, for placing the small gap 531 in communication with the inner space 541.

As described above, the inside of the case 51 is cooled by water supplied from the external supply. Therefore, the static magnetic field forming member 54, the upper and the lower yokes 53 and 55, and the center pole 52 are coated with anitcorrosives or plated with metal on the peripheral surfaces thereof for prevention of corrosion.

With reference now to FIGS. 28 and 29, the probe 5b for transversal waves will be described. In FIGS. 28 and 29, the same reference numerals will be used to denote the same parts as in FIGS. 26 and 27.

The case 51 is a water-tight structure and comprises the side wall 511, the top cover 512, the bottom cover 514, and the ceramic plate 515, as in the case 51 of FIGS. 26 and 27. The side wall 511, the top cover 512, and the portion of the bottom cover 514 connected to the side wall are of a magnetic material such as ferritic stainless steel while the central portion of the bottom cover 514 exclusive of the fitting portion is a non-magnetic material such as SUS304 austenitic stainless steel. The static magnetic field forming member 54 is a permanent magnet generally in the shape of a prism, consisting of a number of small cubes of rare earth magnet material which are tightly secured to each other with the N-poles upward and the S-poles downward and combined into the prism. The static magnetic field forming member 54 has a height a little smaller than the inside depth of the case 51 and a horizontal length approximately one third of the inside diameter of the side wall 511. The static magnetic field forming member 54 is tightly fitted within a holder 59 in the shape of a square copper tube with a bottom. The holder 59 is positioned centrally of the case 51 with the lower surface thereof opposed to the upper surface of the ceramic plate 515 with a small gap therebetween and is fixed to the case 51 by securing an upper flange of the holder 59 by screws to the lower surface of the top cover 512.

The coil 56 is positioned in the small gap between the holder 59 and the ceramic plate 515 and is adhered in a position concentrically with the holder 59 or the static magnetic field forming member 54 to the lower surface of the holder 59 with a high temperature adhesive. The opposite ends of the coil 56 are connected, through the cable 561 extending within the annular space 516 defined between the side wall 511 and the holder 59, to the connector 562 mounted on the top cover 512 for connection to external devices.

The top cover 512 is provided with two long water pipes 57a having the lower ends thereof reaching to near the bottom cover 514 and two short water pipes 57b having the lower ends thereof reaching a little below the top cover 512, which pipes are alternately disposed along the circumferential edge of the cover with an equal angular distance therebetween. The long water pipes 57a are connected with the external water supply (not shown) for introducing water as shown by the arrow into the case 51. The water is discharged through the short water pipes 57b as shown by the arrow.

With reference now to FIGS. 30 and 31, the probe 5c for surface waves will be described. In FIGS. 30 and 31, the same reference numerals will be used to denote the same parts as in FIGS. 26 and 27.

The case 51 is a water-tight structure comprising the side wall 511, the top cover 512, the bottom cover 514, and the ceramic plate 515, as in the cases of FIGS. 26 and 27 and FIGS. 28 and 29. The side wall 511, the top cover 512, and the bottom cover 514 are of non-magnetic steel such as SUS 304. The static magnetic field forming member 54 is a permanent magnet generally in the shape of a prism, consisting of a number of small cubes of rare earth magnet material which are tightly secured to each other with the N- and the S-poles in the horizontal direction and combined into the prism. The static field forming member 54 has the lower yokes 552 adhered to opposite lateral sides thereof and secured to the top cover 512 by means of the screws 531.

The coil 56 is mounted on the ceramic plate 515 with a high temperature adhesive. The coil 56 is, as shown in FIG. 30, a zigzag coil with the distance between legs eqaul to a half of the wavelength to be detected. The opposite ends of the coil 56 extend along the outer surface of the lower yoke 552 for connection to external devices through the connector 562.

The top cover 512 is provided with two long water pipes 57a having the lower ends thereof reaching to near the bottom cover 514 and two short water pipes 57b having the lower ends thereof reaching a little below the top cover 512, which pipes are alternately disposed along the circumferential edge thereof with an equal angular distance therebetween. The long water pipes 57a introduce water from the external water supply (not shown) as shown by the arrow into the case 51. The water is discharged from the case 51 to the outside through the short water pipes 57b as shown by the arrow.

A magnetic circuit of the probe 5a for longitudinal waves consists of the static magnetic field forming member 54, the upper and the lower yokes 53 and 55, and the center pole 52. Since the magnetic flux leaks to the outside from between the center pole 52 and the lower yoke 55, the material being inspected opposed to the bottom cover 514 or the ceramic plate 515 has applied thereto a static magnetic field parallel to the surface of said material.

The magnetic circuit of the probe 5b for transverse waves consists of the static magnetic field forming member 54 and the case 51. Since the magnetic flux leaks to the outside from between the static magnetic field forming member 54 and the peripheral edge of the bottom cover 514 of the case 51, the material being inspected opposed to the peripheral edge of the bottom cover 514 or the ceramic plate 515 has applied thereto a static magnetic field perpendicular to the surface of said material.

The magnetic circuit of the probe 5c for surface waves consists of the static magnetic field forming member 54 and the lower yokes 55. Since the magnetic flux leaks between the two lower yokes 55, the material being inspected opposed to the ceramic plate 515 (coil 56) has applied thereto a static magnetic field parallel to the surface of said material. Since the coil 57 is in a zigzag arrangement and the current flows in opposite directions in two adjacent turns of the coil, eddy currents flow on the surface of the material in opposite directions at a distance of $\lambda/2$ therebetween and the vertical vibration reverses in phase at the distance $\lambda/2$, thereby causing the surface waves.

The probes 5a and 5b operate substantially in the same manner except that the modes of the ultrasonic waves thereof are longitudinal and transverse, respectively, because of the difference in direction of the static magnetic field formed in the material being inspected as described above.

Characteristics of the rare earth magnet material constituting the static magnetic field forming member 54 are: residual magnetic flux density 8.5KG at 0.1T, coercive force 8.25 Oe at 0.1T, maximum energy product 18.0MGO, and highest working temperature 250° C.

The probe having the above-described construction according to the present invention is, when used in the through-transmission method, disposed, as shown in FIG. 13, opposite to the surface of the material 4 to be inspected at a distance of 0.5–50 mm therefrom. In order to maintain the probe spaced a predetermined distance from the material being inspected, the probe may be attached to an appropriate support member or may be provided on the outer peripheral edge of the bottom cover 514 thereof with a heat- and wear-resistant shoe of a suitable thickness for lightly urging the support member toward the material 4 being inspected so as to slide on the obverse or reverse surface of the material 4.

The probe according to the present invention has an outside diameter of 140 mm–160 mm and a height of 60 mm–100 mm. In order to maintain the temperature of the static magnetic field forming member 54 lower than 250° C., the highest working temperature of the rare earth magnet material and to avoid any adverse affect by the heat of the material being inspected which is at a temperature of 800° C.–1200° C., the probe according to the present invention requires cooling water in an amount of only 2–3 liter/minute.

Since the probe according to the present invention uses a permanent magnet, particularly a rare earth magnet, as the static magnetic field forming member, it can provide a static magnetic field as strong as in a prior art probe using an electromagnet using a large amount of electric current and can provide a satisfactory detecting capacity. Since a coil necessary to the electromagnet and a source of power to supply electric current to the coil are unnecessary, the apparatus according to the present invention can be made small in size. In fact, the probe according to the present invention is approximately half the size of the prior art probe. This also makes it possible to provide the probes at lower cost and, particularly when a plurality of probes are used in combination, to increase the flaw detecting density and, accordingly, the inspection accuracy. As for reception sensitivity of the probe according to the present invention, when the material being inspected is at a temperature of 800° C. or higher, while it is approximately 40 dB lower in sensitivity than a probe using a piezo-electric device such as an ultrasonic-electric signal transducer at room temperature, it can provide a sufficient inspection capacity by using an amplifier with a high S/N ratio.

On the other hand, since the probe according to the present invention requires only that a pulse-like high frequency current be applied to the coil 56 to generate ultrasonic waves, unlike the prior art in which a large electric current had to be applied to the coil of the electromagnet to form a static magnetic field, it has substantially no means generating heat within the case, thus reducing the required amount of the cooling water, obviating the need for providing for insulation of the cooling structure, and making the probe itself simpler in construction and smaller in size. Accordingly, the probe is free of the problem of deterioration of the insulation and can be used with a high reliability for a long time.

Further, in the cooling structure of the probe according to the present invention, since the lower ends of the feeding water pipes are at different vertical positions from those of the discharging water pipes, an adequate amount of turbulent flow is produced within the case, thereby increasing the cooling effect. Therefore, the probe according to the present invention can be used for inspecting material at a temperature as high as 1200° C. Even when the probe is used at the upper limit of the temperature, the rare earth magnet material constituting the static magnetic field forming member is held at or below the highest working temperature, thereby maintaining the predetermined magnetic field forming ability stably over a long period of time.

Since the ceramic plate 515 is disposed centrally of the bottom cover 514 in the probe according to the present invention, the electromagnetic coupling thereof with the material being inspected is made tight, thereby generating an effective eddy current on the surface thereof and making it possible to detect efficiently the eddy current generated by the reflected or transmitted ultrasonic wave. The ceramic plate 515 may be replaced when necessary according to the extent of wear. The replacement of the ceramic plate or inspection of the inside of the case can be performed easily since the bottom cover 514 is threadably attached to the side wall 511.

Since the static magnetic field forming member consists of a number of small cubes of rare earth magnet material, generation of eddy current therewithin is suppressed. When the static magnetic field forming member 54 is covered by the holder 59 of copper as in the probe for transverse waves, generation of ultrasonic waves therewithin is effectively suppressed. Industrial Applicability Since the present invention is intended to focus a laser beam onto the surface of a material to be inspected and to receive the ultrasonic wave generated by the incidence of the beam for flaw detection, the invention can avoid the thermal effect from the material being inspected at high temperature and can be used for hot flaw detection of steel material, such as slabs and billets, at high temperature and continuous cast pieces from a casting process and is, accordingly, exceedingly useful in the steel industry.

While we have shown and described specific embodiments of our invention, it will be understood that these embodiments are merely for the purpose of illustration and description and that various other forms may be devised within the scope of our invention, as defined in the appended claims.

We claim:

1. An apparatus for non-contact ultrasonic flaw detection, comprising:
   a laser beam generator for emitting a pulsed laser beam;
   a rotary mirror in the shape of a regular polygonal prism having reflecting surfaces for receiving the laser beam emitted from said laser beam generator and reflecting it onto the surface of the material to be inspected;
   a plurality of electromagnetic ultrasonic probes for a plurality of propagation modes, disposed close to the surface of the material to be inspected and each consisting of a static magnetic field forming member and a detector coil;
   a timing signal generator for generating pulse signal in operative association with the movement of said rotary mirror;
   a scanning control device connected to said probes and said timing signal generator for controlling the turning on-and-off of said electromagnetic ultrasonic probes in response to said pulse signal; and
   a flaw detector connected to said probes for receiving a signal from said probe and displaying the results of the flaw detection.

2. An apparatus for non-contact ultrasonic flaw detection, comprising:
   a laser beam generator for emitting a pulsed laser beam;
   a plurality of half-mirrors and a total reflection mirror disposed substantially in parallel with one another in the path of the laser beam generated by said laser beam generator so as to intersect said laser beam substantially at equal angles;
   a plurality of rotary mirrors disposed in the paths of the portions of the laser beam reflected by said mirrors, respectively, and having driving means connected thereto for changing the angles of the reflecting surfaces of the rotary mirrors relative to the material to be inspected;
   a plurality of electromagnetic ultrasonic probes for a plurality of propagation modes, disposed close to the surface of the material to be inspected and each consisting of a static magnetic field forming member and a detector coil;
   a timing signal generator for generating a pulse signal in operative association with the movement of said rotary mirrors;
   a scanning control device connected to said probes and said timing signal generator for controlling the turning on-and-off of said electromagnetic ultrasonic probes in response to said pulse signal; and
   a flaw detector connected to said probes for receiving signals from said probes and displaying the results of the flaw detection.

3. An apparatus for non-contact ultrasonic flaw detection as set forth in any one of claims 1 and 2, in which at least one of said probes is an electromagnetic ultrasonic probe for transverse waves comprising:
   a sealed case consisting of a top cover and a side wall of a magnetic material, respectively, and a bottom member of a non-magnetic material;
   a permanent magnet having an end thereof connected to the central portion of said top cover and the other end thereof opposed to said bottom member;
   a spiral coil interposed between said bottom member and the other end of said permanent magnet; and
   a tubular member for circulating a cooling medium in said sealed case.

4. An apparatus for non-contact ultrasonic flaw detection as set forth in any one of claims 1 and 2, in which at least one of said probes is an electromagnetic ultrasonic probe for surface waves comprising:
   a sealed case consisting of a top cover, a side wall and a bottom member of a non-magnetic material, respectively;
   a permanent magnet connected to the central portion of said top cover;
   a pair of yokes each having an end thereof connected to the side face of said permanent magnet and the other end thereof opposed to said bottom member;
   a zigzag coil opposed to said bottom member between the other ends of said pair of yokes; and
   a tubular member for circulating a cooling medium in said sealed case.

5. An apparatus for non-contact ultrasonic flaw detection as set forth in any one of claims 1 and 2, in which at least one of said probes is an electromagnetic ultrasonic probe for longitudinal waves comprising:
- a sealed case consisting of a top cover, a side wall and a bottom member of a non-magnetic material, respectively;
- a center pole of a magnetic material having one end thereof connected to the central portion of said top cover and the other end thereof tapered and opposed to said bottom member;
- an annular upper yoke of a magnetic material surrounding an end of said center pole and connected to said top cover;
- an annular permanent magnet attached to the under surface of said annular upper yoke so as to surround the intermediate portion of said center pole;
- an annular lower yoke of a magnetic material attached to the under surface of said permanent magnet so as to surround the other end of said center pole and to oppose to said bottom member;
- a spiral coil interposed between the other end of said center pole and said annular lower yoke; and
- a tubular member for circulating a cooling medium in said sealed case.

6. A method for non-contact ultrasonic detection of flaws, comprising the steps of:
- generating a pulsed laser beam;
- directing the pulsed laser beam to a reflecting surface of a rotary mirror in a direction for causing the laser beam to be reflected from the surface and fall on the surface of a material to be inspected;
- turning said rotary mirror about the axis of rotation thereof for causing the reflected beam to scan the surface of the material and generate ultrasonic waves at a successive plurality of points on the surface of the material;
- detecting the ultrasonic waves which reach a surface of the material after having passed through at least a portion of the material by using a plurality of electromagnetic ultrasonic probes positioned along a surface of the material adjacent said plurality of points, each having a static magnetic field forming member and a detector coil; and
- synchronizing the operation of said probes with the movement of said mirror for relating the ultrasonic waves detected by the respective probes to the ultrasonic waves generated by the pulsed laser beam falling on the points of the surface of the material to be inspected which correspond to the respective probes.

7. A method for non-contact ultrasonic detection of flaws, comprising the steps of:
- generating a pulsed laser beam;
- providing a plurality of half mirrors along the path of the beam in positions to be struck by the laser beam for causing each half mirror to reflect only a portion of the energy of the laser beam and passing the remainder of the energy of the laser beam to the mirrors along the path;
- positioning a rotary mirror in the path of the portion of the laser beam reflected from each half mirror in a position for reflecting the portion of the laser beam onto a portion of the surface of a material to be inspected;
- turning the respective rotary mirrors about the axes of rotation thereof for causing the reflected portions of the laser beam to scan corresponding portions of the surface of the material and generate ultrasonic waves at a successive plurality of points on the surface of the material in each scanned portion of the surface;
- detecting the ultrasonic waves which reach a surface of the material after having passed through at least a portion of the material by using a plurality of electromagnetic probes for each scanned portion of the surface of the material, each probe having a static magnetic field forming member and a detector coil; and
- synchronizing the operation of said probes with the movement of the reflected portions of the laser beam over the respective portions of the surface of the material.

* * * * *